US010501492B2

(12) United States Patent
Mishra et al.

(10) Patent No.: US 10,501,492 B2
(45) Date of Patent: Dec. 10, 2019

(54) ANTIBIOTIC COMPOUNDS (75) Inventors: Prabhu Dutt Mishra, Mumbai (IN); Girish Badrinath Mahajan, Mumbai (IN)

(73) Assignees: National Centre for Polar and Ocean Research (NCPOR), Goa (IN); Foundation for Neglected Disease Research (FNDR), Bangalore (IN)

(*) Notice: Subject to any disclaimer, the term of this patent is extended or adjusted under 35 U.S.C. 154(b) by 0 days.

(21) Appl. No.: 13/393,294

(22) PCT Filed: Aug. 31, 2010

(86) PCT No.: PCT/IB2010/053897
§ 371 (c)(1),
(2), (4) Date: Feb. 29, 2012

(87) PCT Pub. No.: WO2011/027290
PCT Pub. Date: Mar. 10, 2011

(65) Prior Publication Data
US 2012/0156295 A1  Jun. 21, 2012

Related U.S. Application Data (60) Provisional application No. 61/239,186, filed on Sep. 2, 2009.

(51) Int. Cl.
A61K 38/00 (2006.01)
C07K 5/10 (2006.01)
C07D 513/18 (2006.01)
C07K 5/103 (2006.01)

(52) U.S. Cl.
CPC .............. *C07K 5/10* (2013.01); *C07D 513/18* (2013.01); *C07K 5/101* (2013.01); *A61K 38/00* (2013.01)

(58) Field of Classification Search
CPC ........ A61K 35/74; A61K 38/00; C12N 15/76; C07K 5/101; C07K 5/10; C07D 513/18
See application file for complete search history.

(56) References Cited

U.S. PATENT DOCUMENTS 2,982,689 A  5/1961 Donovick et al.

FOREIGN PATENT DOCUMENTS

WO  2007/119201 A2  10/2007

OTHER PUBLICATIONS

Nicolaou et al., (J. Am. Chem. Soc., 2005, 127, 11176-11183).*
Drugs.com entry for Resortin, (Nac No. 13220380, Schuyler, LLC revised on Oct. 1998, available online at: http://www.drugs.com/vet/resortin.html?printable=1).*
Pucci et al., Antimicrobial Agents and Chemotherapy, 2004, p. 3697-3701.*
Nicolaou et al., J. Am. Chem. Soc. 2005, 127, 11176-11183. (Year: 2005).*
Menichetti, F., "Current and emerging serious Gram-positive infections", European Society of Clinical Microbiology and Infectious Diseases, 2005, 11 Suppl. 3, pp. 22-28.
Loddenkemper R., et al., "Strategies against multidrug-resistant tuberculosis", Eur Respir J 2002, 20, Suppl. 36, pp. 66s-77s.
Ebata, M., et al., "Studies on Siomycin I Physiochemical Properties of Siomycins A, B and C", The Journal of Antibiotics, Aug. 1969, pp. 364,368.
Von Hunolstein, C., et al., "Penicillin tolerance amongst non-toxigenic *Corynebacterium diphthericte* isolated from cases of pharyngitis", Journal of Antimicrobial Chemotherapy 2002, 50, pp. 125-128.
Riska, P., et al., "Rapid Film-Based Determination of Antibiotic Susceptibilities of *Mycobacterium tuberculosis* Strains by Using a Luciferase Reporter Phage and the Bronx Box", Journal of Clinical Microbiology, Apr. 1999, vol. 37, No. 4, pp. 1144-1149.

* cited by examiner

*Primary Examiner* — Kaipeen E Yang
(74) *Attorney, Agent, or Firm* — Ladas & Parry LLP (57) ABSTRACT Purified compounds of formula I are described. Compounds include all stereoisomeric forms and all tautomeric forms of the compounds of formula I and pharmaceutically acceptable salts and derivatives. Processes for the production of the antibacterial compounds by fermentation of the microorganism belonging to *Streptomyces* species (PM0626271/MTCC 5447) and to pharmaceutical compositions containing one or more of the novel compounds as active ingredient and their use in medicines for treatment and prevention of diseases caused by bacterial infections are described.

1 Claim, 3 Drawing Sheets

ANTIBIOTIC COMPOUNDS

This is a 371 application of PCT/IN2010/053897 filed on 31 Aug. 2010, entitled "ANTIBIOTIC COMPOUNDS", which was published in the English language on 10 Mar. 2011, with International Publication Number WO 20111027290 A1, and which claims priority from U.S. Patent Application 61/239,186 filed 2 Sep. 2009, the content of which is incorporated herein by reference.

FIELD OF THE INVENTION

This invention relates to novel compounds of Formula I having antibacterial activity. The compounds may be obtained by fermentation of a microorganism belonging to Streptomyces species (PM0626271/MTCC 5447). The invention also includes all stereoisomeric forms and all tautomeric forms of compounds of Formula I and pharmaceutically acceptable salts and derivatives thereof. The present invention further relates to processes for the production of the novel antibacterial compounds and to pharmaceutical compositions containing one or more of the novel compounds as an active ingredient and their use in medicines for treatment and prevention of diseases caused by bacterial infections.

BACKGROUND OF THE INVENTION

The dramatic rise in the prevalence of antibiotic resistance among bacteria currently poses a serious threat to public health worldwide. Of particular concern are infections caused by methicillin-resistant *Staphylococcus aureus* (MRSA), penicillin-resistant *Streptococcus pneumoniae* (PRSP), vancomycin-resistant *Enterococcus* (VRE) (Clin. Microbiol. Infect., 2005, 11, Supplement 3: 22-28) and multi drug resistant (MDR) *Mycobacterium tuberculosis* (Eur. Respir. J., 2002, Supplement 36, 66S-77S).

Thiostrepton, an antibiotic isolated from *Streptomyces azureus*, has been reported to be an effective anti-infective medicine having the same general antibiotic spectrum as penicillin and is used against gram-positive coccal infections (U.S. Pat. No. 2,982,689).

Siomycin, a sulfur-containing peptide antibiotic isolated from *Streptomyces sioyaensis*, has been reported to be active against gram-positive bacteria and mycobacteria with little or no activity against gram-negative bacteria (The Journal Of Antibiotics, 1969, 364-368).

There is a need to discover new compounds, which can be used as drugs to treat patients who are at risk of infection or are infected with bacteria, especially multi drug resistant bacteria such as MRSA, VRE and *Mycobacterium tuberculosis*.

SUMMARY OF THE INVENTION

The present invention relates to novel compounds of Formula I.

The present invention also relates to novel purified compounds of Formula I, isolated from the fermented broth of the microorganism belonging to Streptomyces species (PM0626271/MTCC 5447).

The invention also relates to all stereoisomeric forms and all tautomeric forms of compounds of Formula I and pharmaceutically acceptable salts and derivatives thereof.

The compounds of Formula I, and isomers, pharmaceutically acceptable salts and derivatives thereof, have antibacterial activity and are useful for the treatment or prevention of diseases caused by bacteria, particularly multi drug resistant bacteria such as MRSA, VRE and *Mycobacterium tuberculosis*.

The invention further relates to pharmaceutical compositions comprising one or more of the novel compounds of Formula I, an isomer, a pharmaceutically acceptable salt, or derivative thereof, as an active ingredient for the treatment of diseases caused by bacteria, particularly multi drug resistant bacteria such as MRSA, VRE and *Mycobacterium tuberculosis*.

The present invention further relates to processes for the production of the compounds of Formula I and/or their isomers from the microorganism belonging to Streptomyces species (PM0626271/ MTCC 5447).

DETAILED DESCRIPTION OF THE INVENTION

Before describing the present invention in detail, it has to be understood that this invention is not limited to particular embodiments. It is also to be understood that the terminology used herein is for the purpose of describing particular embodiments only, and is not intended to be limiting.

As used in the specification and claims, the singular forms "a", "an" and "the" include plural references unless the context clearly indicates otherwise.

Unless defined otherwise, all technical and scientific terms used herein have the same meaning as commonly understood by one of the ordinary skill in the art to which the invention belongs.

As used herein, the term "derivative" refers to a compound that is derived from a similar compound or a compound that can be imagined to arise from another compound, if one atom is replaced with another atom or group of atoms.

As used herein, the term "stereoisomer" refers to all isomers of individual compounds that differ only in the orientation of their atoms in space. The term stereoisomer includes mirror image isomers (enantiomers), mixtures of mirror image isomers (racemates, racemic mixtures), geometric (cis/trans or syn/anti or E/Z) isomers, and isomers of compounds with more than one chiral center that are not mirror images of one another (diastereoisomers). The compounds of the present invention may have asymmetric centers and occur as racemates, racemic mixtures, individual diastereoisomers, or enantiomers, or may exist as geometric isomers, with all isomeric forms of said compounds being included in the present invention.

As used herein, the term "tautomer" refers to the coexistence of two (or more) compounds that differ from each other only in the position of one (or more) mobile atoms and in electron distribution, for example, keto-enol and imine-enamine tautomers.

As used herein, the term "fermented broth" refers to a suspension of microbial culture in a nutrient medium containing compounds produced by the microbes during its growth and also having unconsumed nutrients.

As used herein, the term "mutant" refers to an organism or cell carrying a mutation, which is an alternative phenotype to the wild-type.

As used herein, the term "variant" refers to an individual organism that is recognizably different from an arbitrary standard type in that species.

The novel compounds of Formula I are structurally represented by the following formula:

MRSA, VRE and *Mycobacterium tuberculosis*. Compounds of Formula I(a) and Formula I(b) have hitherto unreported structures.

The microorganism, which may be used for the production of the compounds of Formula I(a) and Formula I(b), is a strain of *Streptomyces* species (PM0626271/MTCC 5447), herein after referred to as culture no. PM0626271, isolated from a soil sample collected from Schirmacher Oasis in Antarctic region.

Formula I

Formula I(a):

Formula I(b):

The novel compound of Formula I(a) has the molecular formula $C_{71}H_{83}N_{19}O_{18}S_5$ (molecular weight 1649.5). The novel compound of Formula I(b) has the molecular formula $C_{71}H_{85}N_{19}O_{18}S_5$ (molecular weight 1651.5). The novel compounds of Formula I(a) and Formula I(b) may be characterized by any one or more of their physico-chemical and spectral properties, such as high performance liquid chromatography (HPLC), mass spectrum (MS), infra red (IR) and nuclear magnetic resonance (NMR) spectroscopic data as discussed herein below.

The structure of the novel compounds of Formula I(a) and Formula I(b) has been elucidated and its complete characterization is done by HPLC, high resolution MS (HRMS), IR and NMR spectroscopic data. The compounds of Formula I(a) and Formula I(b) are new antibiotics active against bacteria, particularly multi drug resistant bacteria such as The present invention further provides processes for the production of the compounds of Formula I(a) and Formula I(b) from culture no. PM0626271, comprising the steps of: cultivating the culture no. PM0626271 under submerged aerobic conditions in a nutrient medium containing one or more sources of carbon and one or more sources of nitrogen and optionally nutrient inorganic salts and/or trace elements; isolating the compounds of Formula I(a) and Formula I(b) from the fermented broth; and purifying the compounds of Formula I(a) and Formula I(b) using purification procedures generally used in the related art.

Preliminary identification of culture no. PM0626271, which is the producer of compounds of Formula I(a) and Formula I(b) was performed by examination of its colony morphology, wet mount observations and Gram stain reaction. Microscopic studies on the strain of isolated culture no PM0626271 were carried out on Actinomycete Isolation agar (AS-AIA; details given in Example section) containing 1.5% agar and observations were made at 1, 2 and 3 days of incubation at 25° C.

Growth on AS-AIA containing 1.5% agar develops as 1 mm diameter colonies with white sporulation, scanty yellowish substrate mycelia, slightly raised appearance, no diffusible pigment and back side dark buff in color. Under phase contrast light microscopy, wavy tangles of thin mycelia with sporulated tips are observed at 400× magnification. They are Gram-positive. The free spores are non-motile. The observed morphology classifies this organism as a member of Streptomycetes family.

Culture no. PM0626271 has been deposited with Microbial Type Culture Collection (MTCC), Institute of Microbial Technology, Sector 39-A, Chandigarh-160 036, India, a World Intellectual Property Organization (WIPO) recognized International Depository Authority (IDA) and has been given the accession number MTCC 5447.

In addition to the specific microorganism described herein, it should be understood that mutants, such as those produced by the use of chemical or physical mutagens including X-rays, U.V. rays etc. and organisms whose genetic makeup has been modified by molecular biology techniques, may also be cultivated to produce the compounds of Formula I(a) and Formula I(b).

The screening for suitable mutants and variants which can produce the compound according to the invention can be confirmed by HPLC and/or determination of biological activity of the active compounds accumulated in the fermented broth, for example by testing the compounds for antibacterial activity.

The medium and/or nutrient medium used for isolation and cultivation of culture no. PM0626271, which produces the compounds of Formula I(a) and Formula I(b), preferably contains sources of carbon, nitrogen and nutrient inorganic salts. The carbon sources are, for example, one or more of starch, glucose, sucrose, dextrin, fructose, molasses, glycerol, lactose, or galactose. Preferred carbon sources are soluble starch and glucose. The sources of nitrogen are, for example, one or more of soybean meal, peanut meal, yeast extract, beef extract, peptone, malt extract, corn steep liquor, gelatin, or casamino acids. Preferred nitrogen sources are peptone and yeast extract. The nutrient inorganic salts are, for example, one or more of sodium chloride, potassium chloride, calcium chloride, magnesium chloride, ferric chloride, strontium chloride, cobalt chloride, potassium bromide, sodium fluoride, sodium hydrogen phosphate, potassium hydrogen phosphate, dipotassium hydrogen phosphate, magnesium phosphate, calcium carbonate, sodium bicarbonate, sodium silicate, ammonium nitrate, potassium nitrate, ferrous sulphate, sodium sulphate, ammonium sulphate, magnesium sulphate, ferric citrate, boric acid or trace salt solution. Calcium carbonate, sodium chloride, and magnesium chloride are preferred.

The maintenance of culture no. PM0626271 may be carried out at a temperature ranging from 22° C. to 36° C. and a pH of about 7.5 to 8.0. Typically, culture no. PM0626271 is maintained at 25° C. to 27° C. and a pH of about 7.4 to 7.8. The well-grown cultures may be preserved in the refrigerator at 4° C. to 8° C.

Seed culture cultivation of culture no. PM0626271 may be carried out at a temperature ranging from 25° C. to 36° C. and a pH of about 7.5 to 8.0 for 66 hours to 75 hours at 200 rpm (revolutions per minute) to 280 rpm. Typically, culture no. PM0626271 seed is cultivated at 29° C. to 31° C. and a pH of about 7.4 to 7.8, for 72 hours at 230 rpm to 250 rpm.

The production of the compounds of Formula I(a) and Formula I(b) may be carried out by cultivating culture no PM0626271 by fermentation at a temperature ranging from 26° C. to 36° C. and a pH of about 6.5 to 8.5, for 24 hours to 96 hours at 60 rpm to 140 rpm and 100 lpm (liter per minute) to 200 lpm aeration. Typically, culture no. PM0626271 is cultivated at 30° C. to 32° C. and pH 7.4 to 7.8 for 40 hours to 96 hours at 90 rpm and 110 lpm aeration.

The production of the compounds of Formula I(a) and Formula I(b) can be carried out by cultivating culture no. PM0626271 in a suitable nutrient broth under conditions described herein, preferably under submerged aerobic conditions, for example in shake flasks, as well as in laboratory fermenters. The progress of fermentation and production of the compounds of Formula I(a) and Formula I(b) can be detected by high performance liquid chromatography (HPLC) and by measuring the bioactivity of the fermented broth against *Staphylococci* and/or *Enterococci* species by the known microbial agar plate diffusion assay method. The preferred culture is *Staphylococcus aureus* E710, which is a strain resistant to methicillin, a β-lactam antibiotic reported in the literature, and *Enterococcus faecium* R2 (VRE) which is resistant to vancomycin. In the resulting fermented broth, the compounds of Formula I(a) and Formula I(b) are present in the culture filtrate as well as in cell mass and can be isolated using known separation techniques such as solvent extraction and column chromatography. Thus, the compounds of Formula I(a) and Formula I(b) can be recovered from the culture filtrate by extraction at a pH of about 5 to 9 with a water immiscible solvent such as petroleum ether, dichloromethane, chloroform, ethyl acetate, diethyl ether or butanol, or by hydrophobic interaction chromatography using polymeric resins such as "Diaion HP-20®" (Mitsubishi Chemical Industries Limited, Japan), "Amberlite XAD®" (Rohm and Haas Industries U.S.A.), activated charcoal, or by ion exchange chromatography at pH 5 to 9. The active material can be recovered from the cell mass by extraction with a water miscible solvent such as methanol, acetone, acetonitrile, n-propanol, or iso-propanol or with a water immiscible solvent such as petroleum ether, dichloromethane, chloroform, ethyl acetate or butanol. One other option is to extract the whole broth with a solvent selected from petroleum ether, dichloromethane, chloroform, ethyl acetate, methanol, acetone, acetonitrile, n-propanol, iso-propanol, or butanol. Typically, the active material is extracted with ethyl acetate from the whole broth. Concentration and lyophilization of the extracts gives the active crude material.

The compounds of Formula I(a) and Formula I(b) of the present invention can be recovered from the crude material by fractionation using any of the following techniques: normal phase chromatography (using alumina or silica gel as stationary phase; eluents such as petroleum ether, ethyl acetate, dichloromethane, acetone, chloroform, methanol, or combinations thereof); reverse phase chromatography (using reverse phase silica gel such as dimethyloctadecylsilyl silica gel, (RP-18) or dimethyloctylsilyl silica gel (RP-8) as stationary phase; and eluents such as water, buffers [for example, phosphate, acetate, citrate (pH 2 to 8)], and organic solvents (for example, methanol, acetonitrile, acetone, tetrahydrofuran, or combinations of these solvents); gel permeation chromatography (using resins such as Sephadex LH-20® (Pharmacia Chemical Industries, Sweden), TSK-gel® Toyopearl HW (TosoHaas, Tosoh Corporation, Japan)

in solvents such as methanol, chloroform, acetone, ethyl acetate, or their combinations, or Sephadex® G-10 and G-25 in water); or by counter-current chromatography (using a biphasic eluent system made up of two or more solvents such as water, methanol, ethanol, iso-propanol, n-propanol, tetrahydrofuran, acetone, acetonitrile, methylene chloride, chloroform, ethyl acetate, petroleum ether, benzene, and toluene). These techniques may be used repeatedly, alone or in combination. A typical method is chromatography over normal phase using silica gel.

The compounds of Formula I(a) and Formula I(b) and stereoisomers thereof, can be converted into their pharmaceutically acceptable salts and derivatives which are all contemplated by the present invention.

Salts of the compounds can be prepared by standard procedures known to one skilled in the art, for example, salts like hydrochloride and sulphate salts, can be prepared by treating the compounds of Formula I(a) and Formula I(b) and isomers thereof, with a suitable acid, for example hydrochloric acid, sulphuric acid.

The compounds of Formula I(a) and Formula I(b) have antibacterial activity against a wide range of bacterial strains. The compounds of Formula I(a) and Formula I(b) also have antimycobacterial activity against MDR *Mycobacterium tuberculosis* strains such as *M. tuberculosis* H37Rv; *M. tuberculosis* Clinical isolate—S (Streptomycin), H (Isoniazid or Isonicotinyl hydrazine), R (Rifampicin) and E (Ethambutol)—Resistant; and *M.tuberculosis* Clinical isolate—S, H, R and E sensitive.

One or more of the compounds of Formula I(a) and Formula I(b), stereoisomers and their pharmaceutically acceptable salts thereof, alone or together, can be administered to animals, such as mammals, including humans, as pharmaceuticals and in the form of pharmaceutical compositions. One or more of the compounds of Formula I(a) and Formula I(b), stereoisomers and their pharmaceutically acceptable salts thereof, alone or together, can be administered prophylatically to a patient who is at risk for being infected by a bacterial infection. The patient may be someone who may be exposed to the bacteria in a medical setting such as in a hospital or in other setting where the bacteria may be present.

Accordingly, the present invention also relates to the compounds of Formula I(a) and Formula I(b), their stereoisomers and their pharmaceutically acceptable salts for use as pharmaceuticals and to the use of the compounds of Formula I(a) and Formula I(b), stereoisomers and their pharmaceutically acceptable salts for the manufacture of medicaments having antibacterial activity.

The present invention further relates to pharmaceutical compositions, which contain an effective amount of one or more of the compounds of Formula I(a) and Formula I(b) and/or stereoisomers and/or one or more pharmaceutically acceptable salts and/or derivatives thereof, together with at least one pharmaceutically acceptable excipient or carrier useful for preventing or treating bacterial infections.

The effective amount of the compounds of Formula I(a) and Formula I(b), or its stereoisomers, or its pharmaceutically acceptable salts or its derivatives as the active ingredient in the pharmaceutical preparations normally is from about 0.01 mg to 1000 mg.

The present invention also relates to method of treating or preventing a bacterial infection comprising administering to a mammal in need thereof an effective amount of one or more of the compounds of Formula I(a) and Formula I(b) and/or stereoisomers and/or one or more pharmaceutically acceptable salts thereof.

The present invention also relates to a method for the manufacture of a medicament containing one or more of the compounds of Formula I(a) and Formula I(b) and/or stereoisomers and/or one or more pharmaceutically acceptable salts thereof, for the treatment or prevention of diseases caused by bacterial infections.

The compounds of the present invention are particularly useful as anti-bacterial agents. The present invention accordingly relates to the use of one or more of the compounds of Formula I(a) and Formula I(b) and/or stereoisomers and/or one or more pharmaceutically acceptable salts and/or derivatives thereof, for the manufacture of a medicament for the prevention or treatment of diseases caused by bacterial infections.

The bacterial infections for the treatment of which the compounds of the present invention are used may be caused by bacteria belonging to *Staphylococcus, Streptococcus, Enterococcus, Bacillus* or *Mycobacterium* species. The bacteria belonging to *Staphylococcus* species can be methicillin-resistant or vancomycin resistant. The bacteria belonging to *Enterococci* species can be vancomycin resistant. The bacteria belonging to *Mycobacterium* species can be multi drug-resistant.

The term "*Staphylococcus* species" refers to Gram-positive bacteria, which appear as grape-like clusters when viewed through a microscope and as large, round, golden-yellow colonies, often with β-hemolysis, when grown on blood agar plates. Species of *Staphylococus* include *Staphylococcus aureus*.

The term "*Streptococcus* species" refers to a genus of spherical, Gram-positive bacteria, and a member of the phylum Firmicutes. Streptococci are lactic acid bacteria. *Streptococcus* species includes bacteria such as *S. hemolyticus, S. mitis, S. salivarius, S. pneumoniae*. *Streptococcus* species are responsible for infectious diseases such as meningitis, bacterial pneumonia, endocarditis, erysipelas and necrotizing fasciitis ('flesh-eating' bacterial infections).

The term "*Enterococcus* species" refers to a genus of lactic acid bacteria of the phylum Firmicutes. They are Gram-positive cocci which often occur in pairs (Diplococci for example *Diplococcus pneumoniae*). Enterococci are facultative anaerobic organisms.

The term "*Bacillus* species" refers to a large number of diverse, rod-shaped Gram positive bacteria that are motile by peritrichous flagella and are aerobic such as *B.anthracis, B.subtilis* or anaerobic such as *Clostridium* spp. for example *C.difficile*. These Bacilli belong to division Firmicutes.

The term "*Mycobacterium* species" refers to Gram-positive, non-motile, pleomorphic rods related to the actinomyces. Tuberculosis in humans is caused by *Mycobacterium tuberculosis*. MDR-TB (multi-drug resistant tuberculosis) describes strains of tuberculosis that are resistant to at least the two first-line TB drugs, isoniazid and rifampicin.

The compounds of the present invention can be administered orally, nasally, topically, parenterally such as subcutaneously, intramuscularly, intravenously, or by other modes of administration.

Pharmaceutical compositions which contain one or more of the compounds of Formula I(a) and Formula I(b) or a stereoisomer or a pharmaceutically acceptable salt or a derivative thereof, optionally with other pharmaceutically acceptable excipient or carrier, can be prepared by mixing the active compounds with one or more pharmaceutically acceptable excipients and/or carriers such as, wetting agents, solubilisers such as surfactants, vehicles, tonicity agents, fillers, colorants, masking flavors, lubricants, disintegrants, diluents, binders, plasticizers, emulsifiers, ointment bases, emollients, thickening agents, polymers, lipids, oils, cosolvents, complexation agents, or buffer substances, and converting the mixture into a suitable pharmaceutical form such as, for example, tablets, coated tablets, capsules, granules, powders, creams, ointments, gels, syrup, emulsions, suspensions, or solutions suitable for injection used for parenteral administration.

Examples of excipients and/or carriers that may be mentioned are cremophor, poloxamer, benzalkonium chloride, sodium lauryl sulfate, dextrose, glycerin, magnesium stearate, polyethylene glycol, starch, dextrin, lactose, cellulose, carboxymethylcellulose sodium, talc, agar-agar, mineral oil, animal oil, vegtetable oil, organic and mineral waxes, paraffin, gels, propylene glycol, benzyl alcohol, dimethylacetamide, ethanol, polyglycols, tween 80, solutol HS 15, water and saline. It is also possible to administer the active substances as such, without vehicles or diluents, in a suitable form, for example, in capsules.

As is customary, the galenic formulation and the method of administration as well as the dosage range which are suitable in a specific case depend on the species to be treated and on the state of the respective condition or disease, and can be optimized using methods known in the art. On average, the daily dose of active compound in a patient is 0.0005 mg to 50 mg per kg, typically 0.001 mg to 20 mg per kg.

The following are provided as illustrative examples of the present invention and do not limit the scope thereof.

EXAMPLE 1

Isolation of Culture No. PM0626271 from Soil Collected from Antarctic Region a) Composition of the isolation medium:
Modified artificial sea water agar: Peptone 1.5 g, yeast extract 0.5 g, ferric chloride 0.007 g, 1.0 L water (750 mL artificial sea water+250 mL demineralised water), agar powder 15.0 g, final pH (at 25° C.) 7.4 to 7.8.
Composition of the artificial seawater: Sodium chloride 24.6 g, potassium chloride 0.67 g, calcium chloride.2H$_2$O 1.36 g, magnesium sulphate.7H$_2$O 6.29 g, magnesium chloride.6H$_2$O 4.66 g, sodium bicarbonate 0.18 g, demineralized water 1.0 L, final pH (at 25° C.) 7.8 to 8.2.
b) Procedure:
From Schirmacher Oasis region in Antarctica area, surface level soil was collected and was stored at −20° C. throughout the journey to Piramal Life Sciences Limited, Goregaon, Mumbai, India. The sample was stored at −20° C. to −22° C. and later thawed to room temperature (25±2° C.) for isolation of the microbes. The soil sample (~1 g) was suspended in 25 mL of sterile 1% peptone water in a 100 mL sterilized flask. The flask was vortexed for 30 seconds. Serial dilutions up to 10$^{-5}$ were prepared in sterile 1% peptone water. 100 µL of 10$^{-5}$ dilution was surface spread on modified artificial seawater agar. The plate was incubated at room temperature (25±2° C.) till colonies were observed. After incubation for one and a half month, the colony which appeared on this medium was streaked on petri plates containing actinomycete isolation agar [Hi Media] prepared in 75% artificial sea water [Accumix™] (AS-AIA). The isolate was purified and was provided culture ID number PM0626271. The culture no. PM0626271 was thus isolated from amongst the growing microorganisms as single isolate.

EXAMPLE 2

Purification of Culture No. PM0626271 a) Composition of the purification medium (Actinomycete Isolation Agar, agarified by 1.5% agar agar):
Glycerol 5.0 mL, sodium caseinate 2.0 g, L-asparagine 0.1 g, sodium propionate 4.0 g, dipotassium phosphate 0.5 g, magnesium sulphate 0.1 g, ferrous sulphate 0.001 g, 1.0 L water (750 mL Artificial Sea Water+250 mL demineralised water), agar powder 15.0 g, final pH (at 25° C.) 7.4 to 7.8.
Composition of the artificial seawater: Sodium chloride 24.6 g, potassium chloride 0.67 g, calcium chloride.2H$_2$O, 1.36 g, magnesium sulphate.7H$_2$O 6.29 g, magnesium chloride.6H$_2$O 4.66 g, sodium bicarbonate 0.18 g, demineralized water 1.0 L, final pH (at 25° C.) 7.8 to 8.2.
b) Procedure:
The culture no. PM0626271 was streaked on Actinomycete Isolation Agar (containing 75% artificial sea water salts) petriplate. The petriplate was incubated for 10 days at 25° C. One of the isolated colonies from the petriplate was transferred to fresh slants of Actinomycete Isolation Agar prepared in 75% artificial seawater. The slants were incubated for 10 days at 25° C.

EXAMPLE 3

Maintenance of Producer Strain-Culture No. PM0626271 a) Composition of the medium (Actinomycete Isolation Agar):
Glycerol 5.0 mL, sodium caseinate 2.0 g, L-asparagine 0.1 g, sodium propionate 4.0 g, dipotassium phosphate 0.5 g, magnesium sulphate 0.1 g, ferrous sulphate 0.001 g, 1.0 L water (750 mL artificial sea water+250 mL demineralised water), agar powder 15.0 g, final pH (at 25° C.) 7.4 to 7.8.
Composition of the artificial sea water: Sodium chloride 24.6 g, potassium chloride 0.67 g, calcium chloride.2H$_2$O 1.36 g, magnesium sulphate.7H$_2$O 6.29 g, magnesium chloride.6H$_2$O 4.66 g, sodium bicarbonate 0.18 g, demineralized water 1.0 L, final pH (at 25° C.) 7.8 to 8.2.
b) After dissolving the ingredients thoroughly by heating, the resultant solution was distributed in test tubes and sterilized at 121° C. for 30 minutes. The test tubes were cooled and allowed to solidify in a slanting position. The agar slants were streaked with the growth of culture no. PM0626271 by a wire loop and incubated at 27° C. to 29° C. until a good growth was observed. The well-grown cultures were stored in the refrigerator at 4° C. to 8° C.

EXAMPLE 4

Fermentation of the Culture No. PM0626271 in Shake Flasks a) Composition of seed medium [AS-274 (1)]:
Glucose 15 g, corn steep liquor 5 g, peptone 7.5 g, yeast extract 7.5 g, calcium carbonate 2.0 g, sodium chloride 5.0 g, volume made with 750 mL artificial sea water and 250 mL demineralised water.
b) The above medium was distributed in 40 mL amounts in 500 mL capacity Erlenmeyer flasks and autoclaved at 121° C. for 30 minutes. The flasks were cooled to room temperature (25±2° C.) and each flask was inoculated with a loopful of the well-grown producing strain (culture no. PM0626271)

on the slant and shaken on a rotary shaker for 72 hours at 230 rpm to 250 rpm at 30° C. (±1° C.) to give seed culture.
c) Composition of the production medium [AS 36P (1)]:
Soluble Starch 20 g, glucose 15 g, yeast extract 2 g, peptone 3 g, calcium carbonate 2 g, ammonium sulfate 0.5 g, corn steep liquor 2 g, sodium chloride 2 g, magnesium phosphate 5 g, cobalt chloride 1mL/L from stock of 1 g/L, trace salt solution 1 mL/L, volume made to 1 L using with 75% artificial sea water and 25% demineralised water.
d) 40 mL of the production media in 500 mL capacity Erlenmeyer flasks was autoclaved at 121° C. for 30 minutes, cooled to 29° C. to 30° C. and seeded with 5% (v/v) of the seed culture mentioned in Example 4b.
e) Fermentation parameters:
The production flasks were incubated on shaker at 29° C. and 220 rpm for 96 hours. The production flasks were harvested and the whole broth from each media flask was extracted with equal volume of methanol under shaking condition for one hour at 29° C. and centrifuged at 3500 rpm for half an hour. The supernatant was used for antibacterial agar well diffusion assay for monitoring of the activity.

The production of the compounds of Formula I(a) and Formula I(b) in the fermentation broth was determined by testing the bioactivity against *S. aureus* E710(MRSA strain) and/or *Enterococcus faecium* R2 (VRE) using the agar well diffusion method. The harvest pH of the fermented broth was 7.0 to 8.0. The fermented broth was harvested and the whole broth was used for isolation and purification of the compounds of Formula I(a) and Formula I(b).

EXAMPLE 5

Preparation of Seed Culture in Shake Flasks for Fermentation a) Composition of the medium [AS-274 (1)]:
Glucose 15 g, corn steep liquor 5 g, peptone 7.5 g, yeast extract 7.5 g, calcium carbonate 2.0 g, sodium chloride 5.0 g, volume made with 750 mL Artificial Sea Water and 250 mL demineralised water.
b) The above medium was distributed in 200 mL amounts in 1000 mL Erlenmeyer flasks and autoclaved at 121° C. for 30 minutes. The flasks were cooled to room temperature (25±2° C.) and each flask was inoculated with a loopful of the well-grown producing strain (PM0626271) on the slant and shaken on a rotary shaker for 70 hours to 74 hours at 230 rpm to 250 rpm at 29° C. to 30° C. to obtain the seed culture.

EXAMPLE 6

Cultivation of the Culture No PM0626271 in Fermenter a) Composition of the production medium:
Artificial Sea Water (artificial sea water salt 28.32 g) (75%), soluble starch 20 g, glucose 15 g, yeast extract 2 g, peptone 3 g, calcium carbonate 2 g, ammonium sulphate 0.05 g, corn steep liquor 2 g, sodium chloride 2 g, magnesium phosphate 5 g, cobalt chloride (cobalt chloride 1 g demineralized water 1.0 L) 1 mL/L, trace salt solution (copper sulphate 7 g, ferrous sulphate 1 g, manganese chloride 8 g, zinc sulphate 2 g, demineralized water 1.0 L) 1 mL/L, demineralized water 1.0 L, pH 6.5 to 7.5 (before sterilization).
b) 100 L of the production medium in 150 L fermenter along with 30 mL of desmophen as an antifoaming agent was sterilized in situ for 30 minutes at 121° C., cooled to 29° C. to 30° C. and seeded with 2.5 L to 3.5 L of the seed culture obtained above (Example 5).
c) Fermentation parameters: The fermentation was carried out at temperature 29° C. to 30° C., agitation 100 rpm, aeration 60 lpm and harvested at 70 hours to 74 hours. The production of the compounds of Formula I(a) and Formula I(b) in the fermentation broth was detected qualitatively by testing the bioactivity against *S. aureus* E710 (MRSA strain) and/or *Enterococcus faecium* R2 (VRE) using the agar well diffusion method. The harvest pH of the fermented broth was 7.5 to 8.0. After the harvest, whole broth was subjected to solvent extraction.

EXAMPLE 7

Isolation and Purification of the Compounds of Formula I(a) and Formula I(b)

Figure 1:
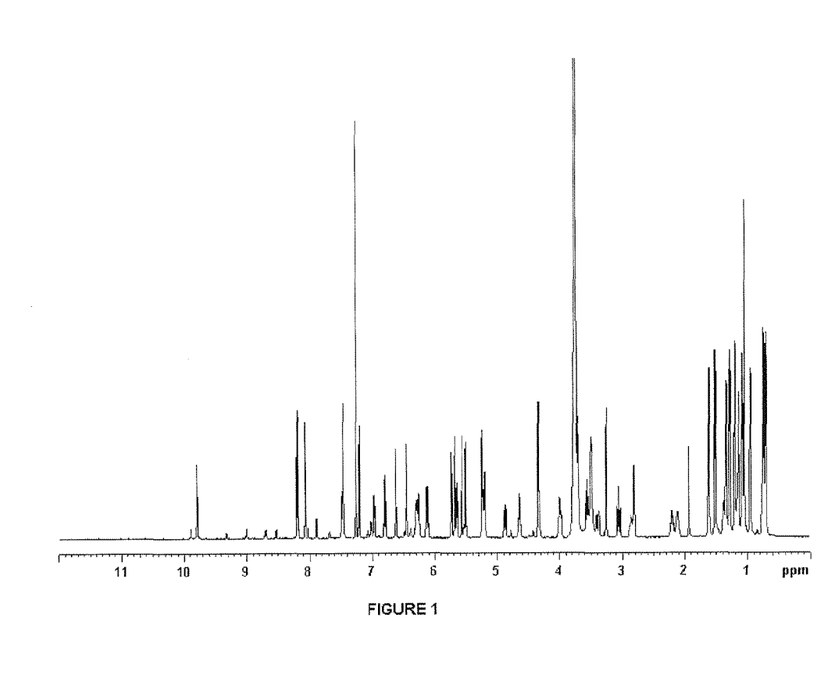
FIG. 1 Illustrates the $^1$H NMR spectrum (500 MHz; Instrument Bruker) of compound of Formula I(a) in $CDCl_3$: $CD_3OD$ (4:1).
Figure 2:
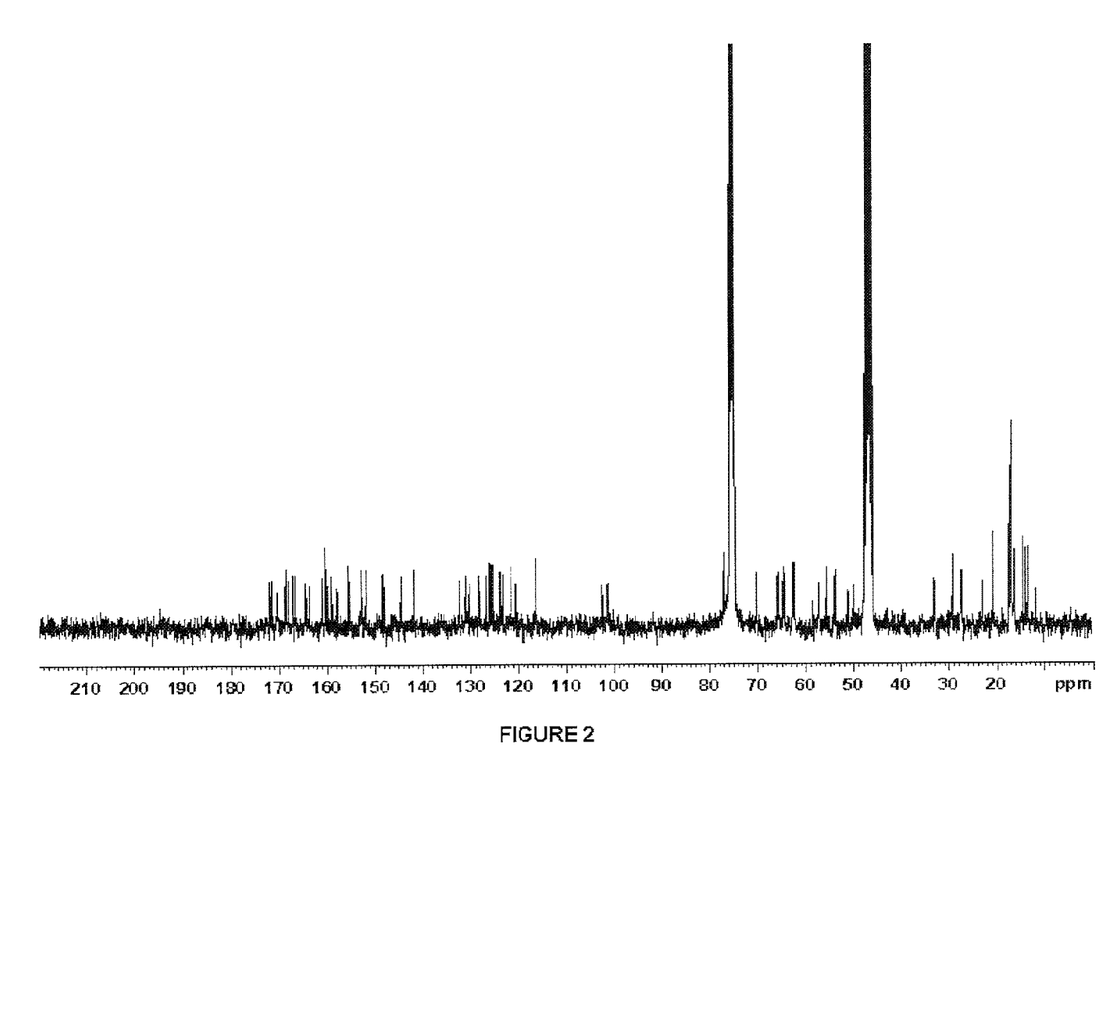
FIG. 2 Illustrates the $^{13}$C NMR spectrum (75 MHz; Instrument Bruker) of compound of Formula I(a) in $CDCl_3$: $CD_3OD$ (4:1).

The whole broth (10 L batch) was extracted using ethyl acetate (1:1). The organic and aqueous layers were separated. The organic layer was processed to evaporate the solvent to obtain crude ethyl acetate extract (1.5 g). The crude extract was further processed by flash chromatography (silica gel, 30 g, solvent: methanol/chloroform step gradient, flow: 15 mL/minute). The active compound eluted with 1% methanol to 5% methanol in chloroform, which was concentrated to obtain the semipure compound (250 mg). Further purification was carried out by repeated normal phase preparative HPLC.
Preparative HPLC Conditions:
  Column: Eurospher silica (10μ, 20×250 mm)
  Eluent: methanol:chloroform (5:95)
  Flow rate: 20 mL/minute
  Detection (UV): 245 nm
  Retention time: compound of Formula I(a) (5 to 6 minutes), compound of Formula I(b) (8 to 10 minutes)
Purity of fractions was checked by bioassay against *E. faecium* R2 and/or *S. aureus* 3066 and/or analytical HPLC. The eluates containing the compounds of Formula I(a) and Formula I(b) were pooled and concentrated under reduced pressure to remove the solvent to obtain compound of Formula I(a) (40 mg), and compound of Formula I(b) (3 mg).
Analytical HPLC Conditions:
  Column: Eurospher RP-18, (3μ, 4.6×125 mm)
  Solvent system: Gradient (0% acetonitrile to 100% in 15 minutes against water, followed by 100% acetonitrile for 5 minutes)
  Flow rate: 1 mL/minute
  Detection (UV): 245 nm
  Retention time: compound of Formula I(a) (12 to 13 minutes), and compound of Formula I(b) (11 to 12 minutes)
A. Physical & Spectral Properties of the Compound Compound of Formula I(a):
  Appearance: White powder
  Melting point: 240° C. (decomposes)
  Solubility: Soluble in chloroform, ethyl acetate, methanol and insoluble in water
  MS [HR-ESI(+) MS)] m/z: 1650.4858 (M+H)
  Molecular weight: 1649.5
  Molecular formula: $C_{71}H^{83}N_{19}O_{18}S_5$
  IR (KBr): 3386, 2927, 1648, 1507, 1206, 756, 666 cm$^{-1}$
  $^1$H NMR: refer to Table 1 and FIG. 1
  $^{13}$C NMR: refer to Table 2 and FIG. 2

B. Physical & Spectral Properties of the Compound of Formula I(b):

Appearance: White powder

Solubility: Soluble in chloroform, ethyl acetate, methanol and insoluble in water MS [HR-ESI(+) MS)] m/z: 1674.4787 (M+Na)

Molecular weight: 1651.50

Figure 3:
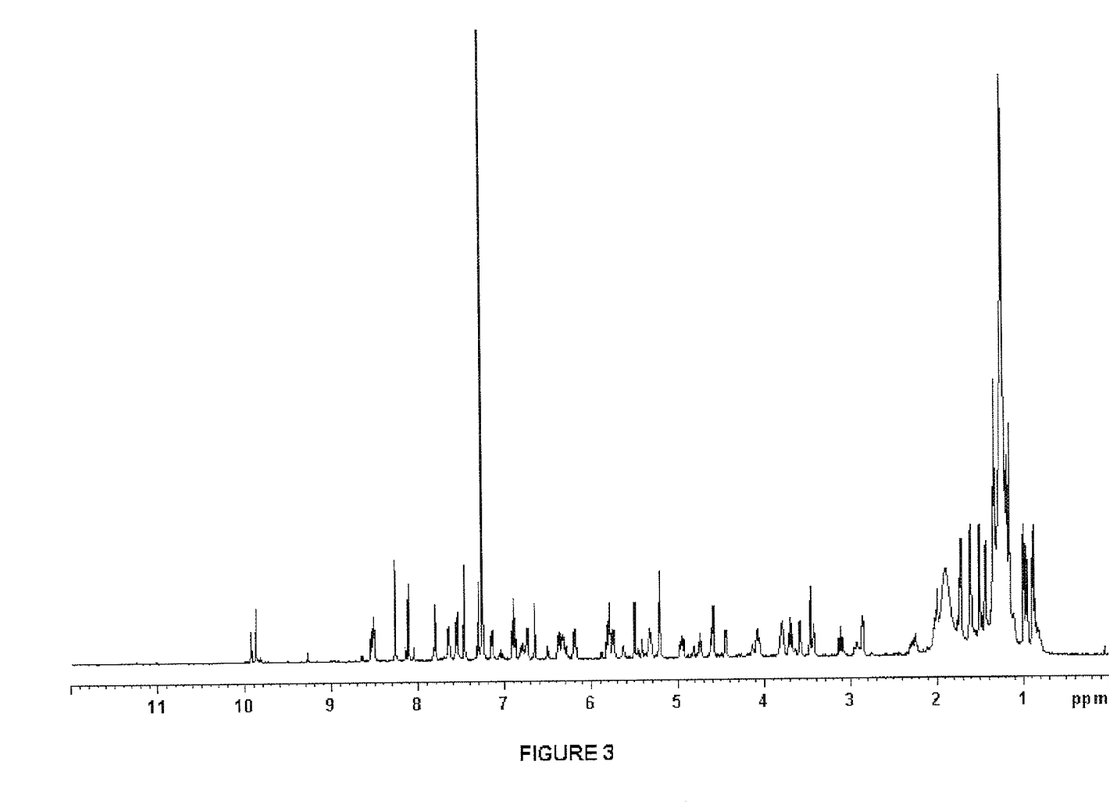
FIG. 3 Illustrates the $^1$H NMR spectrum (500 MHz; Instrument Bruker) of compound of Formula I(b) in $CDCl_3$: $CD_3OD$ (4:1).

Molecular formula: $C_{71}H_{85}N_{19}O_{18}S_5$ $^1$H NMR: refer to Table 3 and FIG. 3

TABLE 1

$^1$H NMR of the compound of Formula I(a) in CDCl$_3$: CD$_3$OD (4:1) at 500 MHz

| Peak | δ |
|---|---|
| 1 | 0.7 (d, 3H) |
| 2 | 0.74 (d, 3H) |
| 3 | 0.95 (d, 3H) |
| 4 | 1.04 (s, 3H) |
| 5 | 1.08 (d, 3H) |
| 6 | 1.2 (d, 3H) |
| 7 | 1.28 (d, 3H) |
| 8 | 1.34 (d, 3H) |
| 9 | 1.37 (m, 1H) |
| 10 | 1.5 (d, 3H) |
| 11 | 1.6 (d, 3H) |
| 12 | 2.1 (m, 1H) |
| 13 | 2.2 (m, 1H) |
| 14 | 2.2 (m, 1H) |
|  | 3.99 (m, 1H) |
| 15 | 2.8 (d, 1H) |
| 16 | 3.05 (t, 1H) |
|  | 3.5 (t, 1H) |
| 17 | 3.49 (d, 2H) |
| 18 | 3.67 (d, 1H) |
| 19 | 3.7 (q, 1H) |
| 20 | 4.33 (d, 1H) |
| 21 | 4.33 (d, 1H) |
| 22 | 4.62 ((q, 1H) |
| 23 | 4.86 (dd, 1H) |
| 24 | 5.19 (s, 1H) |
| 25 | 5.19 (s, 1H), |
|  | 5.67 (s, 1H) |
| 26 | 5.2 (t, 1H) |
| 27 | 5.6 (d, 1H) |
| 28 | 5.62 (s, 1H), |
|  | 6.44 (s, 1H) |
| 29 | 5.65 (d, 2H) |
| 30 | 5.72 (s, 1H), |
|  | 6.61 (s, 1H) |
| 31 | 6.1 (q, 1H) |
| 32 | 6.25 (m, 1H) |
| 33 | 6.28 (d, 2H) |
| 34 | 6.8 (d, 1H) |
| 35 | 6.91 (s, 1H) |
| 36 | 6.94 (s, 1H) |
| 37 | 7.2 (s, 1H) |
| 38 | 7.43 (s, 1H) |
| 39 | 7.45 (s, 1H) |
| 40 | 7.65 (s, 1H) |
| 41 | 7.87 (s, 1H) |
| 42 | 8.05 (s, 1H) |
| 43 | 8.17 (s, 1H) |
| 44 | 8.2 (s, 1H) |
| 45 | 8.5 (s, 1H) |
| 46 | 8.67 (s, 1H) |
| 47 | 8.99 (s, 2H) |
| 48 | 9.72 (s, 1H) |
| 49 | 9.8 (s, 1H) |

TABLE 2

$^{13}$C NMR of the compound of Formula I(a) in CDCl$_3$: CD$_3$OD (4:1) at 75 MHz

| Signal | δ |
|---|---|
| 1 | 12.11 |
| 2 | 13.74 |
| 3 | 14.1 |
| 4 | 14.8 |
| 5 | 16.48 |
| 6 | 17.11 |
| 7 | 17.27 |
| 8 | 17.55 |
| 9 | 20.9 |
| 10 | 23.13 |
| 11 | 27.56 |
| 12 | 27.56 |
| 13 | 29.04 |
| 14 | 33.24 |
| 15 | 46.17 |
| 16 | 50.14 |
| 17 | 51.3 |
| 18 | 53.91 |
| 19 | 53.91 |
| 20 | 55.8 |
| 21 | 57.32 |
| 22 | 58.8 |
| 23 | 62.42 |
| 24 | 62.73 |
| 25 | 64.45 |
| 26 | 64.73 |
| 27 | 65.69 |
| 28 | 65.95 |
| 29 | 70.27 |
| 30 | 77.1 |
| 31 | 101.45 |
| 32 | 101.45 |
| 33 | 102.6 |
| 34 | 116.52 |
| 35 | 120.63 |
| 36 | 121.59 |
| 37 | 123.28 |
| 38 | 123.87 |
| 39 | 123.87 |
| 40 | 125.48 |
| 41 | 126.03 |
| 42 | 126.69 |
| 43 | 128.24 |
| 44 | 130.34 |
| 45 | 130.98 |
| 46 | 131.14 |
| 47 | 132.39 |
| 48 | 141.85 |
| 49 | 144.61 |
| 50 | 148.17 |
| 51 | 148.45 |
| 52 | 151.89 |
| 53 | 152.76 |
| 54 | 155.45 |
| 55 | 157.9 |
| 56 | 159.0 |
| 57 | 160.04 |
| 58 | 160.36 |
| 59 | 161.01 |
| 60 | 163.75 |
| 61 | 164.46 |
| 62 | 164.5 |
| 63 | 166.6 |
| 64 | 167.13 |
| 65 | 167.95 |
| 66 | 168.47 |
| 67 | 168.67 |
| 68 | 170.35 |
| 69 | 170.35 |
| 70 | 171.63 |
| 71 | 172.0 |

TABLE 3

$^1$H NMR of the compound of Formula I(b) in CDCl$_3$: CD$_3$OD (4:1) at 500 MHz

| Peak | δ |
|---|---|
| 1 | 0.88 (d, 3H) |
| 2 | 0.95 (d, 3H) |
| 3 | 0.99 (d, 3H) |
| 4 | 1.0 (m, 1H) |
| 5 | 1.16 (s, 3H) |
| 6 | 1.18 (d, 3H) |
| 7 | 1.32 (d, 3H) |
| 8 | 1.35 (d, 3H) |
| 9 | 1.43 (d, 3H) |
| 10 | 1.5 (d, 3H) |
| 11 | 1.61 (d, 3H) |
| 12 | 1.72 (d, 3H) |
| 13 | 2.02 (m, 1H) |
| 14 | 2.28 (m, 1H) |
| 15 | 2.8 (d, 1H) |
| 16 | 3.17 (t, 1H) |
|    | 3.69 (t, 1H) |
| 17 | 3.43 (d, 1H) |
| 18 | 3.46 (d, 1H) |
| 19 | 3.58 (d, 1H) |
| 20 | 3.8 (q, 2H) |
| 21 | 4.06 (m, 1H) |
| 22 | 4.45 ((d, 1H) |
| 23 | 4.59 (t, 1H) |
| 24 | 4.61 (dd, 1H) |
| 25 | 4.74 (t, 1H) |
| 26 | 4.95 (t, 1H) |
| 27 | 5.19 (s, 1H), |
|    | 5.78 (s, 1H) |
| 28 | 5.19 (s, 1H) |
| 29 | 5.3 (d, 1H) |
| 30 | 5.52 (s, 1H), |
|    | 6.65 (s, 1H) |
| 31 | 5.65 (s, 1H) |
| 32 | 5.72 (d, 1H) |
| 33 | 5.8 (d, 1H) |
| 34 | 6.1 (q, 1H) |
| 35 | 6.34 (m, 1H) |
| 36 | 6.36 (d, 1H) |
| 37 | 6.73 (d, 1H) |
| 38 | 6.91 (d, 1H) |
| 39 | 6.94 (s, 1H) |
| 40 | 7.14 (s, 1H) |
| 41 | 7.3 (s, 1H) |
| 42 | 7.46 (s, 1H) |
| 43 | 7.54 (d 1H) |
| 44 | 7.65 (d, 1H) |
| 45 | 7.80 (s, 1H) |
| 46 | 8.05 (s, 1H) |
| 47 | 8.11 (s, 1H) |
| 48 | 8.14 (s, 1H) |
| 49 | 8.26 (s, 1H) |
| 50 | 8.52 (t, 1H) |
| 51 | 8.65 (d, 1H) |
| 52 | 9.2 (s, 1H) |
| 53 | 9.87 (s, 1H) |
| 54 | 9.92 (s, 1H) |

Biological Evaluation of the Compounds of Formula I(a) and Formula I(b)
In-vitro Assays

EXAMPLE 8

The in-vitro potency was established by minimum inhibitory concentration (MIC) determinations of the compounds of Formula I(a) and Formula I(b) against bacterial strains, by using the Macro-broth dilution method as per National Committee for Clinical Laboratory Standards (2000) guidelines (Methods for Dilution Antimicrobial Susceptibility Tests for Bacteria that Grow Aerobically—Fifth Edition: Approved Standard M7-A5. NCCLS, Wayne, Pa., USA). Mueller-Hinton broth was used as nutrient medium for the assay, unless stated otherwise. PM181104 (PCT publication no. WO2007119201) was used as known standard in all in-vitro experiments. For preparation of the stock solution the compounds of Formula I(a) and Formula I(b) were dissolved in chloroform (5% of the total required volume) and diluted using methanol (95% of the total required volume).

Result:

The results obtained are shown in Table 4 and Table 5, and demonstrate that the compounds of Formula I(a) and Formula I(b) have utility in treating bacterial infections.

TABLE 4

MICs of the compound of Formula I(a) against bacterial strains

| Test Organism | MIC (µg/ml) | Test Organism | MIC (µg/ml) |
|---|---|---|---|
| S. aureus C1 MRSA 2 | 0.25 | S. aureus E712, MRSA Erythro$^R$, 59 | 0.25 |
| S. aureus C1 MRSA 3 | 0.25 | S. aureus 503, MRSA, 62 | >1 |
| S. aureus C1 MRSA 5 | 0.25 | S. aureus SG 511, MRSA, 63 | 1 |
| S. aureus C1 MRSA 7 | 0.125 | S. aureus 789, MRSA, 64 | >1 |
| S. aureus C1 MRSA 8 | 0.25 | S. aureus 209 P, MSSA | 0.063 |
| S. aureus C1 MRSA 9 | 0.25 | S. epidermidis 823, Teicho$^R$, 230 | 0.25 |
| S. aureus C1 MRSA 10 | 0.25 | S. epidermidis 6098, Erythro$^R$, 233 | >1 |
| S. aureus C1 MRSA 13 | 0.25 | S. epidermidis 6729 II W, Erythro$^R$, 236 | 0.125 |
| S. aureus C1 MRSA 16 | 0.25 | S. epidermidis 2361 W, 246 | 0.25 |
| S. aureus C1 MRSA 17 | 0.125 | S. epidermidis 4264 I (1) W, 247 | 0.125 |
| S. aureus C1 MRSA 20 | 0.125 | S. epidermidis Pat 01 IV, 251 | 0.25 |
| S. aureus C1 MRSA 21 | 0.125 | E. faecium C1 VRE 26 | 0.25 |
| S. aureus C1 MRSA 22 | 0.25 | E. faecium C1 VRE 27 | 0.25 |
| S. aureus C1 MRSA 23 | 0.016 | E. faecium C1 VRE 28 | 0.125 |
| S. aureus C1 MRSA 24 | 0.25 | E. faecium C1 VRE 31 | 0.5 |
| S. aureus C1 MRSA 25 | 0.15 | E. faecium C1 VRE 33 | 0.125 |
| S. aureus KEM MRSA 1 | 0.25 | E. faecium C1 VRE 34 | 0.25 |
| S. aureus KEM MRSA 2 | 0.25 | E. faecium KEM VRE 1 | 0.25 |
| S. aureus KEM MRSA 3 | 0.25 | E. faecium KEM VRE 2 | 0.5 |
| S. aureus KEM MRSA 4 | 0.125 | E. faecium KEM VRE 3 | 0.25 |
| S. aureus KEM MRSA 5 | 0.125 | E. faecium KEM VRE 4 | 0.5 |
| S. aureus MRSA 3 lilavati | 0.125 | E. faecium KEM VRE 5 | 0.25 |
| S. aureus Misk MRSA 35 | 0.125 | E. faecium R-2 (VRE), | 0.25 |
| S. aureus Misk MRSA 37 | 0.125 | Enterococcus faecium, VSE (322) | 0.125 |
| S. aureus Misk MRSA 38 | 0.125 | Bacillus cereus (121) | 0.031 |
| S. aureus E710, MRSA | 0.125 | Bacillus subtilis ATCC 6633 (123) | 0.031 |
| S. aureus ATCC 33591, MRSA | 0.125 | Bacillus megaterium FH1127 (124) | 0.125 |

TABLE 5

MICs of the compounds of Formula I(a) and Formula I(b) against bacterial strains

| | Minimal Inhibitory Concentration (µg/ml) | |
|---|---|---|
| Test culture | Compound of Formula I(a) | Compound of Formula I(b) |
| E. faecium, R-2 (VRE) | 0.125 | 2 |
| S. aureus E710, (MRSA) | 0.125 | 2 |
| S. aureus 209P (MSSA) | 0.064-0.125 | 0.25-0.5 |

Abbreviations used in Table 4 and Table 5 are -

TABLE 5-continued

MICs of the compounds of Formula I(a) and Formula I(b) against bacterial strains

| Test culture | Minimal Inhibitory Concentration (µg/ml) | |
|---|---|---|
| | Compound of Formula I(a) | Compound of Formula I(b) |

S: *Staphylococcus*
E: *Enterococci*

EXAMPLE 9

Evaluation of Antimycobacterial Activity

The assay was done as reported in J. Clin. Microbiol., 1999, 37, 1144. 50 µL of bacterial (as mentioned in Table 6) suspension, equivalent to MacFarlands no. 2 standard (corresponding to >5×10$^7$ CFU/ml) (Remel, Lenexa, Kans.) was added to 400 µL of G7H9 with and without compounds of Formula I(a) and Formula I(b) (tested at 0.5 µg/mL, 5 µg/mL and 10 µg/mL) and incubated for 72 hours at 37° C. After incubation 50 µL of the high titer Luciferase reporter phage (phAE 129) and 40 µL of 0.1M calcium chloride (CaCl$_2$) were added to all the vials and this set up was incubated for 4 hours at 37° C. After incubation 100 µL of the mixture was taken from each vial into a luminometer cuvette and equal amount of working D-luciferin (0.3 mM in 0.05 M sodium citrate buffer, pH 4.5) solution was added. The Relative Light Units (RLUs) were measured after 10 seconds of integration in the Luminometer (Monolight 2010).

Duplicate readings were recorded for each sample and the mean was calculated. The percentage reduction in the RLU was calculated for each test sample and compared with control. The experiment was repeated when the mean RLU of the control was less than 1000. The criterion for activity is antimycobacterial activity indicated by fifty percent reduction in RLU in the presence of the compound in comparison with compound free control.

TABLE 6

Antimycobacterial activity of the compounds of Formula I(a) and Formula I(b)

| Strain | Compounds | % reduction in RLU | | |
|---|---|---|---|---|
| | | 0.5 µg/mL | 5 µg/mL | 10 µg/mL |
| *M. tuberculosis* H$_{37}$Rv | Compound of Formula I(a) | 36.36 | 77.17 | 83.76 |
| | Compound of Formula I(b) | 28.87 | 54.83 | 76.73 |
| Clinical isolate: S, H, R and E resistant | Compound of Formula I(a) | 20.88 | 78.11 | 88.42 |
| | Compound of Formula I(b) | 5.67 | 70.9 | 83.74 |

Conclusion: The compounds of Formula I(a) and Formula I(b) are active against standard strain of TB (H$_{37}$ RV) and MDR *Mycobacterium tuberculosis* strains [resistant to 4 standard antibiotics: S (Streptomycin), H (Isoniazid or Isonicotinyl hydrazine), R (Rifampicin) and E (Ethambutol)].

Formula I(a):

R = (acrylamide structure with CH$_2$, NH$_2$)

Formula I(b):

R = (alanine amide structure with CH$_3$, H, NH$_2$)

We claim:

1. A process for the production of pharmaceutically acceptable salt of compound of Formula I(a) or pharmaceutically acceptable salt of compound of Formula I(b) comprising the steps of:

(a) cultivating the microorganism *Streptomyces* species (PM0626271/MTCC 5447) under submerged aerobic conditions in a nutrient medium containing sources of carbon, nitrogen and inorganic salts at a temperature ranging from 26° C. to 36° C. and a pH of 6.5 to 8.5 for 24 hours to 96 hours at 60 revolutions per minute (rpm) to 140 rpm and 100 litres per minute (lpm) aeration to produce the compound of Formula I(a) and the compound of Formula I(b) in the fermented broth;

(b) isolating the compound of Formula I(a) and the compound of Formula I(b) from the fermented broth obtained after cultivating the microorganism *Streptomyces* species (PM 0626271/MTCC 5447);

(c) purifying the isolated compound of Formula I(a) and the isolated compound of Formula I(b); and (d) converting the purified compound of Formula I(a), or the purified compound of Formula I(b) prepared in step (c) to its pharmaceutically acceptable salt.

* * * * *